(12) United States Patent
Quinn et al.

(10) Patent No.: US 12,119,124 B2
(45) Date of Patent: *Oct. 15, 2024

(54) SYSTEMS AND METHODS FOR HOLISTICALLY AND DYNAMICALLY MANAGING METABOLOMICS

(71) Applicants: Thomas Gregory Quinn, Oakland, CA (US); Venkateswara Rao Vaddineni, San Jose, CA (US); Allan Day Sapp, Gardnerville, NV (US); Daphna Karen Dror, Belmont, CA (US); Stephen Raskin, Oakland, CA (US); Susan Miriam Brand, Richmond, CA (US); Randi Gallenson, Oakland, CA (US)

(72) Inventors: Thomas Gregory Quinn, Oakland, CA (US); Venkateswara Rao Vaddineni, San Jose, CA (US); Allan Day Sapp, Gardnerville, NV (US); Daphna Karen Dror, Belmont, CA (US); Stephen Raskin, Oakland, CA (US); Susan Miriam Brand, Richmond, CA (US); Randi Gallenson, Oakland, CA (US)

(73) Assignee: MedChefs, Inc., Oakland, CA (US)

( * ) Notice: Subject to any disclaimer, the term of this patent is extended or adjusted under 35 U.S.C. 154(b) by 814 days.

This patent is subject to a terminal disclaimer.

(21) Appl. No.: 15/967,268

(22) Filed: Apr. 30, 2018

(65) Prior Publication Data

US 2018/0315511 A1 Nov. 1, 2018

Related U.S. Application Data

(60) Provisional application No. 62/492,925, filed on May 1, 2017.

(51) Int. Cl.
*G16H 80/00* (2018.01)
*G16H 20/30* (2018.01)
(Continued)

(52) U.S. Cl.
CPC ............. *G16H 80/00* (2018.01); *G16H 20/30* (2018.01); *G16H 20/60* (2018.01); *G16H 20/90* (2018.01); *G16H 50/30* (2018.01); *G16B 50/00* (2019.02)

(58) Field of Classification Search
CPC ........ G16H 20/60; G16H 80/00; G16H 50/00; G16H 50/20; G16H 50/30; G16H 50/50;
(Continued)

(56) References Cited

U.S. PATENT DOCUMENTS

| 6,179,778 B1 * | 1/2001 | Leonov | G16H 70/20 600/300 |
| 2003/0091964 A1 * | 5/2003 | Yeager | G16H 20/60 434/127 |

(Continued)

*Primary Examiner* — Jesse P Frumkin
(74) *Attorney, Agent, or Firm* — Kang S. Lim

(57) ABSTRACT

The present invention relates to systems and methods for holistically and dynamically managing metabolomics, leading to improvement of users' overall health. A metabolomics enhancement ("ME") system recommends a metabolomic regiment harmonizing macronutritional and micronutritional consumption for a metabolomics beneficiary. The ME system receives characteristics and palate preferences of the beneficiary. Using the personalized data, the ME system generates a customized dynamic combination of macronutrients and micronutrients for enhancing beneficiary metabolomics, and then transposes the macronutrients and micronutrients combination into a recommended pabulum combination for the metabolomic beneficiary.

25 Claims, 17 Drawing Sheets

(51) Int. Cl.
*G16H 20/60* (2018.01)
*G16H 20/90* (2018.01)
*G16H 50/30* (2018.01)
*G16B 50/00* (2019.01)

(58) Field of Classification Search
CPC ........ G16H 50/70; G16H 50/80; G16H 20/90; G16H 20/30; G06F 19/30; G06F 19/32; G06F 19/34; G06F 19/3456; G06F 19/3462; G06F 19/3468; G06F 19/3475; G06Q 50/22; G06Q 50/24; G16B 50/00; G16B 50/10; G16B 50/20; G16B 50/30; G16B 50/40; G16B 50/50; G16B 99/00
See application file for complete search history.

(56) References Cited

U.S. PATENT DOCUMENTS

| | | | |
|---|---|---|---|
| 2003/0225731 A1* | 12/2003 | Vidgen | G16H 20/60 |
| 2006/0240150 A1* | 10/2006 | Delaney | A23L 33/16 |
| | | | 426/74 |
| 2009/0076903 A1* | 3/2009 | Schwarzberg | G06Q 30/0217 |
| | | | 705/14.19 |
| 2009/0077007 A1* | 3/2009 | Schwarzberg | G06Q 30/02 |
| 2009/0144081 A1* | 6/2009 | Harlan | G06Q 10/10 |
| | | | 705/2 |
| 2009/0222282 A1* | 9/2009 | Ordovas | G16H 10/40 |
| | | | 705/2 |
| 2009/0234839 A1* | 9/2009 | Angell | G06Q 10/04 |
| 2013/0216982 A1* | 8/2013 | Bennett | A61B 5/4866 |
| | | | 434/127 |
| 2015/0206413 A1* | 7/2015 | Warner | G16H 40/63 |
| | | | 340/573.1 |
| 2016/0256108 A1* | 9/2016 | Yun | A61B 5/4884 |
| 2018/0032698 A1* | 2/2018 | Lau | G16H 20/60 |
| 2019/0259489 A1* | 8/2019 | De Petris | G16H 40/67 |
| 2022/0406215 A1* | 12/2022 | Quinn | G09B 19/0092 |

* cited by examiner

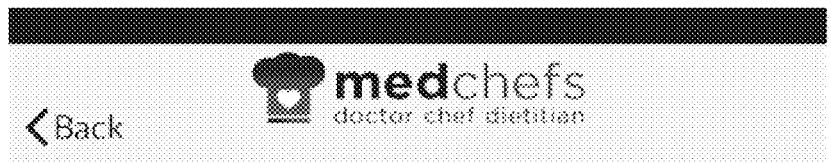

PROFILE (continued)

CURRENT DIETARY HABITS

FRUITS & VEGETABLES
How much fruit and vegetables do you eat per day?
- None
- < 1 cup
- 1-2 cups
- 3-4 cups
- > 4.5 cups WHOLE GRAINS
How much whole grain food do you eat per day?
- None
- 1 serving or less
- 1 - 2 serving
- 2 - 3 serving
- >3 serving Salt
Do you add salt to your food?
- Yes
- No SWEETENED BEVERAGES
How much sweetened beverages (soda, juice, sports drink) did you drink per week?

FIG. 3C

RESOURCES

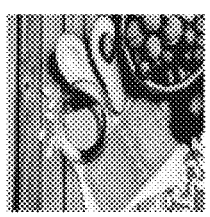
Fats: The Good and the B...
Fat is a general name for a type of macronutrient that along with protein and carbohydrates provide energy for our Read more

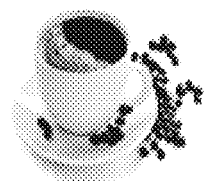
Morning Java?
Coffee, after water, is the most widely consumed beverage in the United States, and is the principal source of caffeine Read more

Meat and Paleo
The Paleo Diet is rich in meat, poultry, seafood, fruits, vegetables, with no grains, refined white flour or sugar and Read more

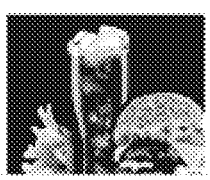
Eating-out Perils
Two out of three Americans are now overweight or obese and the fast food industry may be part of the

    

FIG. 3L

SYSTEMS AND METHODS FOR HOLISTICALLY AND DYNAMICALLY MANAGING METABOLOMICS

CROSS REFERENCE TO RELATED APPLICATIONS

This non-provisional application claims priority to U.S. Provisional Application No. 62/492,925 filed May 1, 2017, of the same title, which application is incorporated herein in its entirety by this reference

BACKGROUND

The present invention relates to systems and methods for holistically and dynamically managing metabolomics, leading to improvement of users' overall health.

While modern medicine has progressed steadily, with many novel cures and treatments continually emerging, a key challenge of providing widespread healthcare has remained. This challenge is the provision of healthcare in a cost-effective manner to the general population.

As Dr. Andrew Weil, a pioneering proponent of integrative medicine, stated, modern medicine is very well suited for treating acute symptoms. Dr. Weil also wisely acknowledges that, modern medicine, despite the rigorous application of the "scientific method," has not been great at promoting preventative paradigms.

Ironically, diverse cultures, perhaps by necessity, have been somewhat more successful in the realm of preventative paradigms such as lifestyle and dietary practices. However, the inconsistent level of quality control in, for example, herbal remedies, sometimes results in poor outcomes and occasionally harmful outcomes.

More recently, there been several attempts at lowering heath care cost by promoting "one size fits all" dietary regimens, such as high protein diets and detox diets. For the most part, these diets have been passing fads because they do not work well for the long-term maintenance of health.

It is therefore apparent that an urgent need exists for a holistic, preventive and dynamic approach to metabolomic management based on solid science. Such an improved approach will enable users to tailor metabolomic regimens by integrating best practices and knowledge into novel paradigms thereby substantially improving their long term health and resulting quality of life.

SUMMARY

To achieve the foregoing and in accordance with the present invention, systems and methods for holistically and dynamically managing metabolomics is provided. In particular the systems and methods for balancing macronutrients and/or micronutrients consumption with resulting metabolomic benefits.

In one embodiment of the MedChefs Ecosystem, eating habits, food preferences and/or dislikes of metabolomic beneficiaries are used to create a unique palate "signature." With each metabolomic beneficiary palate signature, a customized healthy metabolomic regiment can now be extracted from a comprehensive nutrition database. The individualized metabolomic regiment can be presented in many forms such as delicious and yet healthy meal plans, grocery lists, and recipes, customized for each beneficiary. Such an individualized paradigm substantially increases the probability of beneficiary compliance and hence improved health and quality of life.

In some embodiments, the healthy metabolomic regiment may be supplemented with nutrition-related advice and other health enhancing information, including but not limited to food supplements, exercise, meditation and sleep.

In some embodiments, the MedChefs Ecosystem includes NutriTracker enabling beneficiaries to edit/compute MedChefs Core5 and MedChefs Advantage Points, and maintain journals for tracking food consumption and/or inform third parties. The MedChefs Ecosystem can also provide additional resources such as nutrition and exercise related information compiled from scientific literature.

In one embodiment, a metabolomics enhancement ("ME") system recommends a metabolomic regiment for harmonizing macronutritional and micronutritional consumption for a metabolomics beneficiary. The ME system begins by receiving beneficiary characteristics, e.g., personal profile, and palate preferences associated with the beneficiary.

With this personalized data, the ME system generates a customized dynamic combination of macronutrients and micronutrients for enhancing metabolomics of the beneficiary based on the beneficiary characteristics, and then transposes the combination of macronutrients and micronutrients into a recommended pabulum combination. These personalized recommendations are provided to the metabolomic beneficiary.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 3A-3H, 3J-3N and 3P are screenshots illustrating the functionality of the embodiment of MedChefs Ecosystem of FIG. 1.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Figure 1:
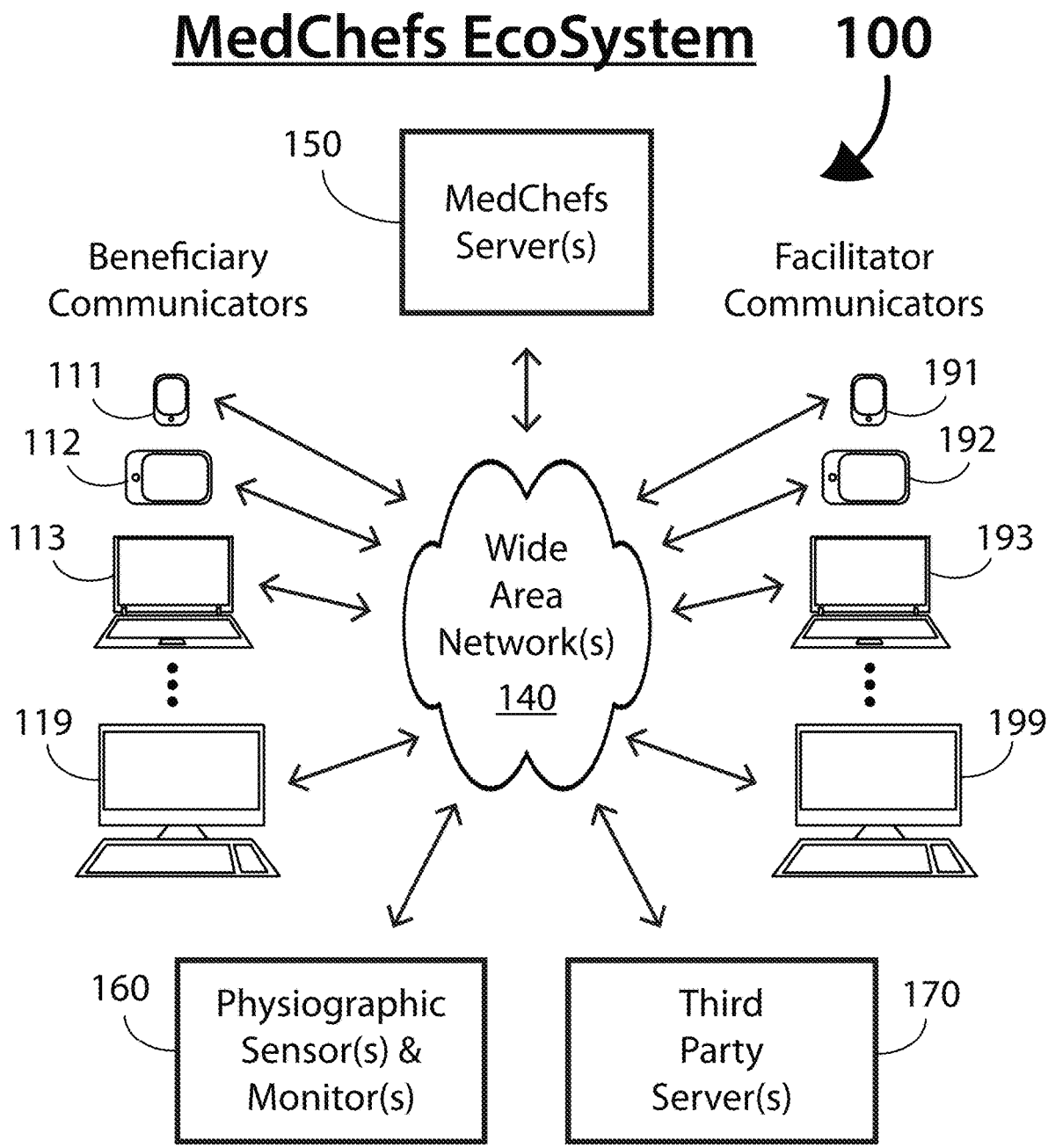
FIG. 1 is a block diagram showing one embodiment of a MedChefs Ecosystem, in accordance with the present invention.

To facilitate discussion, FIG. 1 is a block-diagram of an exemplary MedChefs Ecosystem 100 illustrating systems and methods for holistically and dynamically managing metabolomics for a plurality of beneficiaries (not shown) over wide area networks 140 (WANs) via any of a wide assortment of electronic network terminal devices, e.g., Beneficiary Communicators 111, 112, 113, . . . 119 and Facilitator Communicators 191, 192, 193, . . . 199. In the process of describing various exemplary embodiments, particular attention may be placed upon visual displays on mobile communication devices such as smart phone 111. It is also contemplated that communications can be accomplished with many alternate forms of consumer electronic networked devices including, but not limited to, computers, tablet computer systems, e-reader devices, and virtually any electronic device which includes networking capability and a user interface.

While specific examples of visual user interfaces are described in great detail, MedChefs Ecosystem 100 may be implemented with a wide range of interface types, including any combination of a visual display, tactile and audio output and a visual, tactile or acoustic user interface (UI). Further, although the Internet is a well-known convenient channel for communication between beneficiaries and facilitators, Ecosystem 100 may also utilize equivalent communication over other WANs using services such as, but not limited to, Public Switched Telephone Network (PSTN), Voice over Internet Protocol (VoIP), Skype, WhatsApp, Facebook, SnapChat and Twitter.

Exemplary Communicators, 111-119 and 191-199 represent the multiplicity of devices that can support access to MedChefs Server(s) 150 of Ecosystem 100. Often these communication devices are mobile devices—i.e., devices that can be carried easily from place to place by a beneficiary or a facilitator—typically with Wi-Fi or cellular data or other wireless connectivity and in numerous instances with built-in mobile telephone capability. However, less portable or fixed installation terminals may also support access to MedChefs Server(s) 150.

In addition to managing the nutritional needs of beneficiaries, MedChefs Ecosystem 100 can adaptably enable a wide range of functionality such as: to advertise and offer Nutrition-related Goods and Services (NGS), accumulate independent third-party assessments and reviews, display credentials, leverage the draw of a centralized need-targeted electronic directory, offer informative mini-tutorials and FAQs, update and display availability status, prequalify prospective beneficiaries, provide repeatable direct beneficiary-facilitator communication, arrange for commercial transactions, facilitate and track progress towards consummating commercial transactions, consummate transactions for NGS, follow-up post-transaction with beneficiaries to encourage and enhance good-will, and measure and evaluate the effectiveness of the foregoing and make adjustments and refinements. Some of the supplemental functionality of MedChefs Ecosystem 100 can be supported by third parties resources via for example Third Party Server(s) 170.

Accordingly, MedChefs Ecosystem 100 provides a unified adaptable facility for beneficiaries, to prequalify, locate, evaluate, make repeatable contact with, and acquire NGS, from, one or more nutritional facilitators. NGS can also include nutritional advice and nutrition related information from the facilitators and/or third parties, which may or may not be vetted and/or certified by the MedChefs Ecosystem 100.

Nutritional beneficiaries can be any member(s) of the general population, ranging from healthy toddlers to Alzheimer patients in nursing homes. Beneficiaries can be served as individuals or in groups, including families and communities such as sororities, fraternities, cooperatives, neighborhoods and/or communes. Nutritional facilitators include, but are not limited, to physicians (MDs and DOs), nurse practitioners, pharmacists, nurses, physiotherapists, chiropractors, herbalists, nutritionists, dieticians, caregivers, chefs, food suppliers, delivery services, trainers and motivators.

Referring again to FIG. 1, exemplary Beneficiary Physiologic Sensors and/or Monitors 160 include both personal and communal devices such as sphygmomanometers, metabolic monitors (e.g., blood glucose monitors/sensors and insulin pumps), hydration monitors/sensors, cholesterol monitors/sensors and endothelial function assessors.

Other potentially useful sensors include thermometers, oximeters, and renal function devices liver function monitors capable of measuring, for example, enzymatic liver function capacity and plasma disappearance rate (PDR).

In addition, food, ranging from raw basic ingredients to complete meals, can also be tracked electronically, with the aid of for example RFID scanners, barcode scanners, and cameras.

Figure 2:
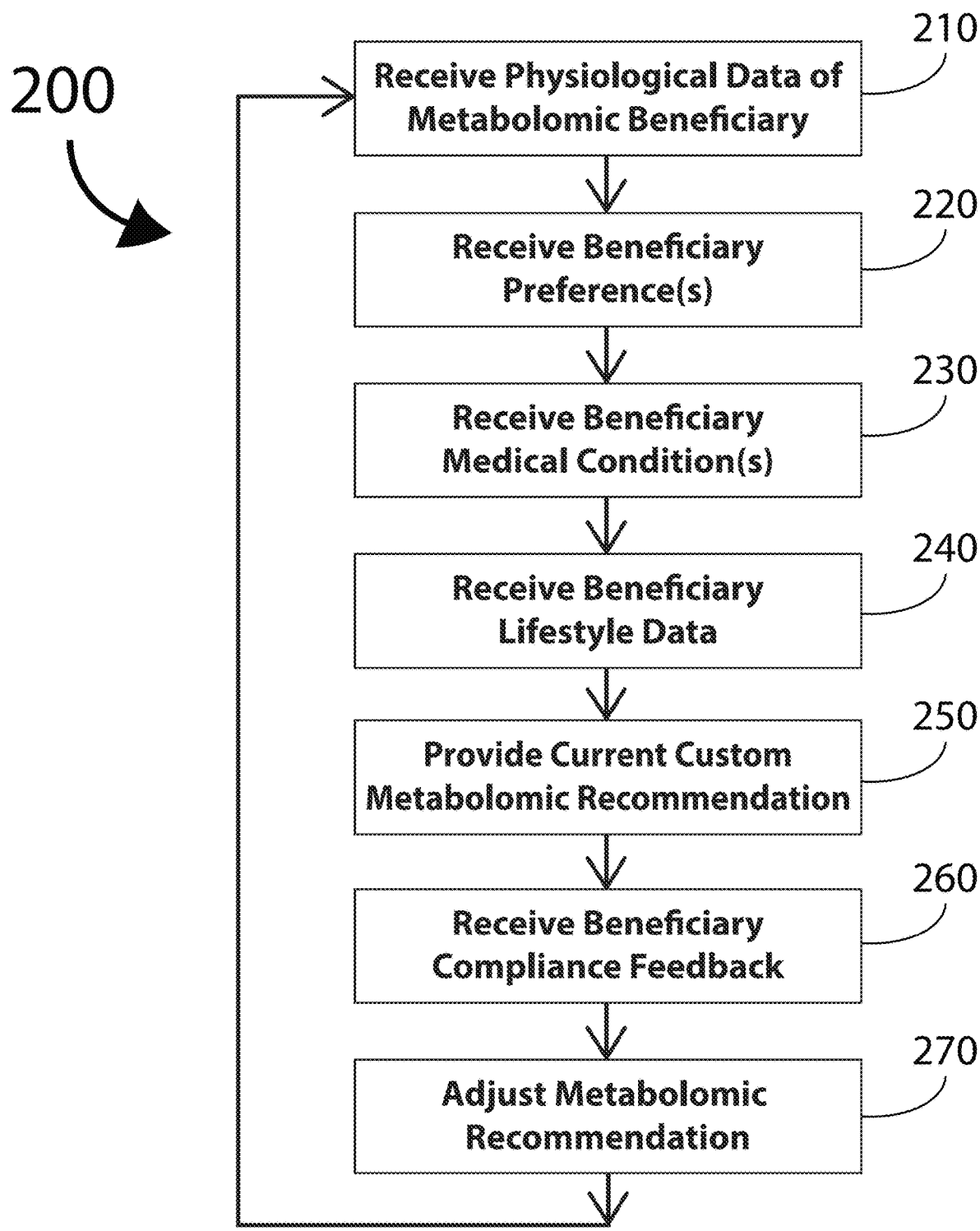
FIG. 2 is a flow diagram illustrating the functionality of the embodiment of the MedChefs Ecosystem of FIG. 1.
Figure 3A:
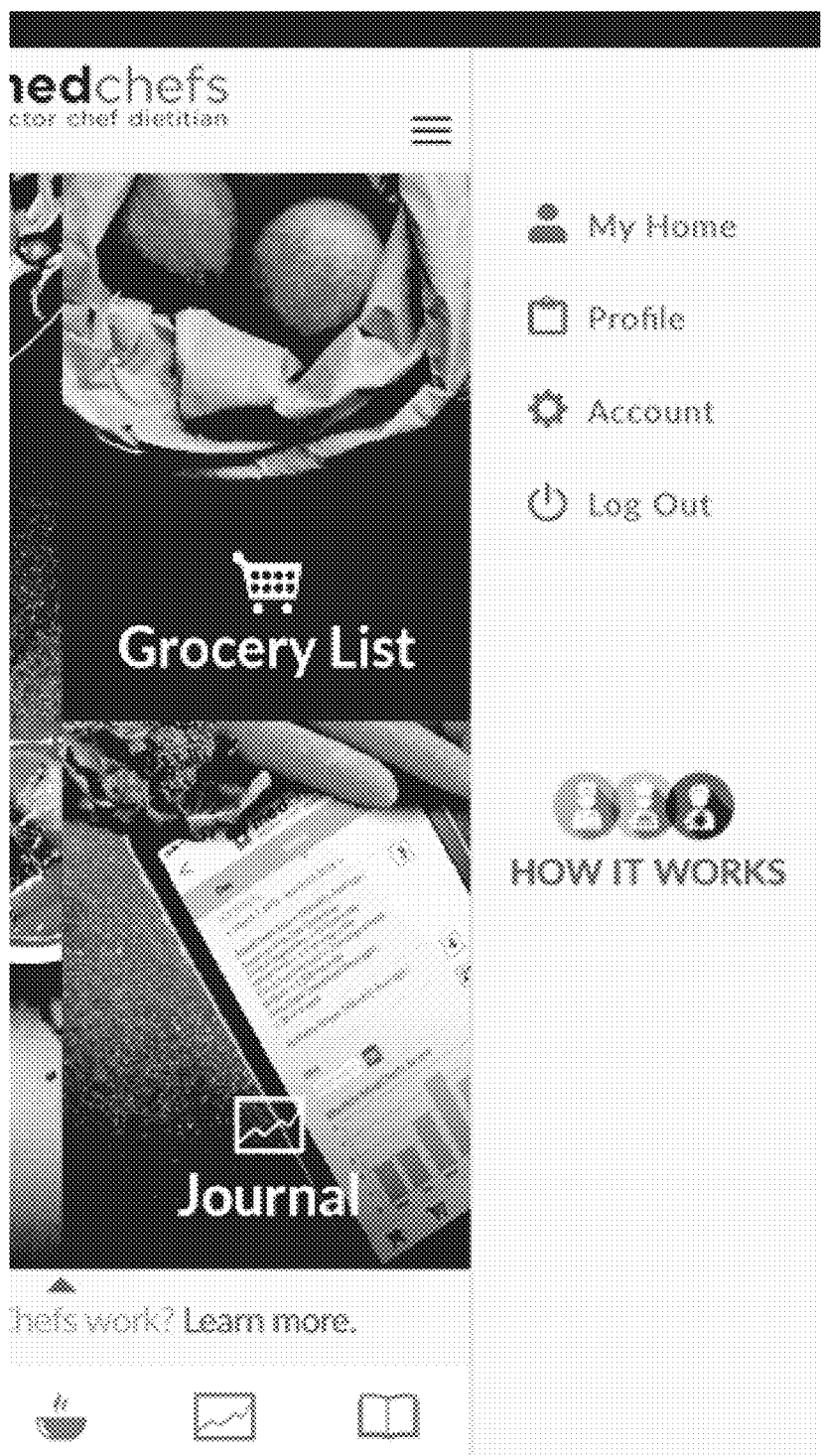

The flow diagram of FIG. 2 and the screenshots 300A-300H, 300J-300N and 300P of FIGS. 3A-3H, 3J-3N and 3P, illustrate the functionality of MedChefs Ecosystem 100, and more specifically the user interfaces of MedChefs Server(s) 150, accessible by beneficiaries and/or facilitators via one or more of Communicators 111-119 and 191-199, respectively. Screenshot 300A of FIG. 3A shows an exemplary home page suitable for display to a nutritional beneficiary (not shown) and/or the beneficiary's caregiver on a smart phone 111 or a tablet 112.

Figure 3B:
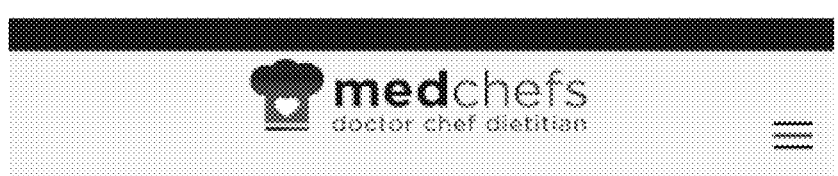
Figure 3B:
Figure 3D:
Figure 3F:
Figure 3F:
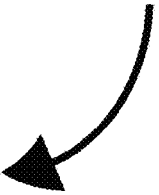

Referring to screenshot 300B of FIG. 3B, the beneficiary/caregiver can inputs the beneficiary's personal profile and lifestyle data, including age, gender, height, weight, body mass index (BMI), activity level, and smoking status (see steps 210 and 240). Other potentially useful, objective and pertinent personal information may include DNA profile (e.g., nucleal and mitochondrial DNA), ethnicity, and/or ancestry.

Awareness of the geographic location and/or climate of the metabolomic beneficiary may also be helpful. For example, the difference of the number of sunny days at various latitudes in combination with altitudes and weather affects one's ability to generate Vitamin D via skin exposure to sunlight. Each beneficiary's unique lifestyle can also affect her/his ability to generate Vitamin D, For example, one who hikes, jogs or swims outdoors will be exposed to more natural sunlight.

In most countries, location can be derived from a postal code such as ZIP code in the U.S.A. or the cell phone GPS signal. Awareness of the beneficiary's locality can also enable MedChefs Ecosystem 100 to optimize for overall freshness and/or cost of the metabolomic recommendation, by taking into consideration seasonality and/or availability of the food ingredients.

As shown in step 230, the MedChefs Server(s) 150 can also be configured to receive the beneficiary's pertinent medical condition(s) such as hypertensive disorder, insulin resistance, diabetes, lipid disorder, thyroid disorder, adrenal disorder, and autoimmune disorder, including risk factors of such condition(s). Other pertinent personal information received by MedChefs Server(s) 150 can include past and current treatment of medical condition(s) such as cancers therapies and procedures.

Using these personalized characteristics, the MedChefs Server(s) 150 can now compute a healthy combination of macronutrients and micronutrients customized for each metabolomic beneficiary. In other words, a proper balance of macronutrients and micronutrients is vital in maintaining health of every metabolomic beneficiary. The MedChefs Ecosystem 100 serves as a tool for adjusting macronutrient and micronutrient consumption to address unique health care requirements. This novel strategy is in stark contrast with known simplistic one-size-fits-all diet programs emphasizing caloric intake.

Hence, in accordance with various embodiments of the present invention, these individualized metabolomic regiments provide each metabolomic beneficiary with recommendations focused on the consumption of healthy foods preferred by the individual metabolomic beneficiary. Portion control is indirectly accomplished through the highly personalized recommendations and education.

Macronutrients include carbohydrates (both natural and processed), proteins (including essential amino acids), fats (including cholesterol and lipids), and fiber. Generally, carbohydrates can be found in grains and grain-based products such as pasta, pastry and breads, while proteins and fats can be found in meats and seafood. Fiber can be found in fruits and vegetables. Note that although plants include protein, vegetarian diets should carefully balance plant consumption to assure a proper mix of amino acids. Using this strategy, the MedChefs Ecosystem 100 can also be beneficial to vegetarians and/or vegans.

Micronutrients include vitamins, minerals, trace elements, amino acids and other organic compounds such as folic acid, carotenoids and antioxidants. For example, vitamins A, B1, B2, B3, B4, B5, B6, B7, B12, C, D, E and K, iron, calcium, iodine, fluoride, Recommendations to the metabolomic beneficiaries can also take into consideration, for example, W.H.O. guidelines for healthy range of sugar consumption, and avoidance of unhealthy foods such as foods containing trans-unsaturated fatty acids; genetically-modified and/or highly processed food with preservatives commonly found in cured meats and packaged snacks such as potato chips.

In accordance with the present invention, various embodiments of MedChefs Ecosystem 100 can be tuned to one or more goals, primary, primordial prevention and/or secondary prevention for the metabolomic beneficiaries.

Primordial prevention: the prevention of the emergence of Risk Factors in a healthy population. For example: dietary services could prevent the development of hypertension or diabetes.

Primary prevention: the prevention of emergence of Disease in those that may be at risk. For example: preventing stroke or myocardial infarction by consuming proper dietary pattern in those with risk factors such as hypertension.

Secondary prevention: the prevention of Subsequent or Recurrent Events in those already with a defined disease process. For example, for those that have suffered a myocardial infarction (heart attack) a proper dietary pattern can prevent a second heart attack.

Hence, with the primordial/primary prevention goals in mind, for example, metabolomic protocols such as one based on a Mediterranean Dietary Pattern provides optimal population-based health outcomes for metabolomic beneficiaries. This exemplary metabolomic protocol includes:
>4.5 cups of fruits and vegetables per day;
>3 servings of whole grains per day;
at least 2 servings of fish per week;
<1,500 mg of sodium per day;
<36 ounces of sweet beverages per week;
<2 servings per week of processed meats; and
>25 grams of dietary fiber for women, >38 grams of dietary fiber for men.

Such metabolomic protocols provide the requisite macro and micronutrients for optimum health for primordial and primary prevention. Accordingly, in certain subsets for primary and secondary prevention, healthcare providers may find the MedChefs Ecosystem 100 very useful as a tool for "dialing in" more precise macro or micronutrient manipulation to address unique healthcare needs of the individual beneficiary metabolomic.

Using this flexible and multifaceted approach, MedChefs Ecosystem 100 is able to service a very wide range of metabolomic beneficiaries, each beneficiary with a unique profile and/or circumstance(s). In addition, adjustments can be made for individual conditions or circumstances of the individual metabolomic beneficiaries, including but not limited to pregnancy, recovery from illness, injury, surgery or medical chronic conditions such as diabetes, osteoporosis and/or hypertension.

In one example, Beneficiary A is 36-year-old healthy female Professor of Pharmacology. She weighs 135 pounds and is 5' 6" in height. Her BMI is 22. She practices yoga three times a week at the campus gym, and jogs the equivalent of three miles twice a week on an elliptical treadmill. She is three months pregnant. She is mildly allergic to peanuts and grass pollen. She is lactose intolerant. Her ancestry is 50% Native American and 50% Korean. Her paternal grandfather was diagnosed with type 2 diabetes at age 50. She works lives in the greater Boston area and shops for most of her groceries at Wholefoods™, Costco™, Trader Joes™ and Blue Apron™. Most days, she prefers to bring her own lunch so she has time to work on her novel. She eats out every Saturday evening at a local Italian or Japanese restaurant with her family.

In another diverse example, Beneficiary B is a 62-year-old male retired fire captain who lives with his wife in Anchorage, Alaska where they grew up. He weighs 195 pounds and is 6' 1" in height. He meditates five times a week, and hikes a couple of time a week weather permitting. He loves fishing and smokes his own salmon. He is allergic to penicillin. His ancestry is 50% Irish and 50% Italian. His maternal grandmother had a mild stroke at age 64. Both of his parents are in their 90s and they reside at a local assisted care facility. Two years ago, he was diagnosed with Stage 2 Non-Hodgkin Lymphoma and is currently responding well to monthly immunotherapy as an outpatient at a teaching hospital. He has moderate hypertension with a BP of 140/90 and a resting pulse rate of 75. They shop at a local Safeway™ and eat out at a steakhouse twice a week. They both love gardening and enjoy growing organic vegetables in their climate-controlled greenhouse.

In screenshots 300C-300F of FIGS. 3C-3F, the beneficiary/caregiver can continue by inputting the beneficiary's nutritional preference(s) and/or habit(s) (see step 220). Examples of preferences include meats such as beef and poultry, fish such as salmon and tuna, dairy such as cheese and yogurt, and vegetables such as broccoli and cabbage. Beneficiary preferences may also include dietary classifications such as gluten-free, vegan and vegetarian, and/or religious preferences such Kosher and Halal. Beneficiary dietary habits can include higher level choices of general food sources such as meats versus seafood, or number of meals per day and size of each serving. The profile of the beneficiary can be supplemented by medical condition(s) such as allergies to both food types and/or drugs, as exemplified in screenshot 300F.

Figure 3G:
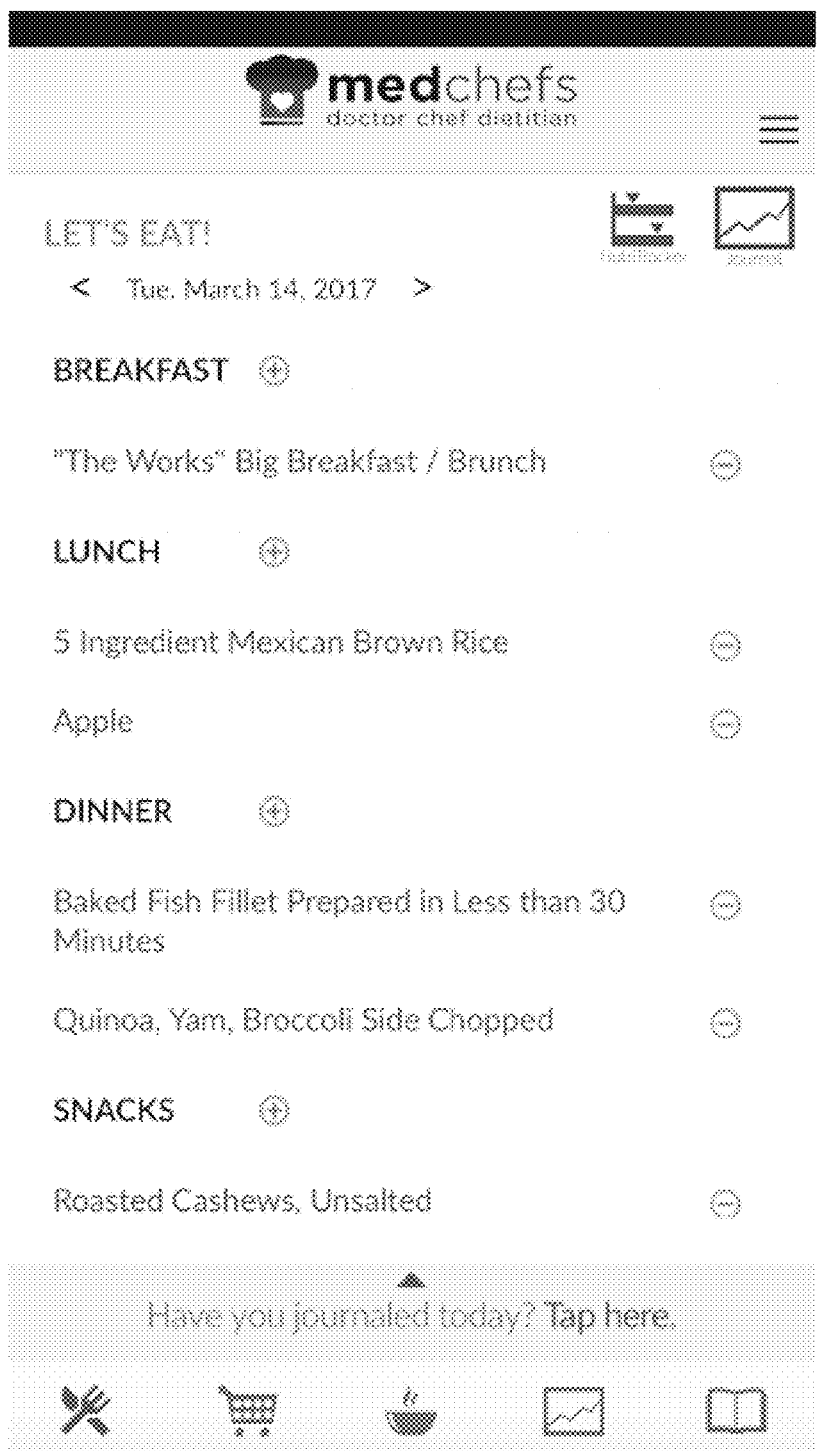

By compiling and taking into consideration the beneficiary's profile, lifestyle, nutritional preference(s) and/or habit(s), MedChefs Server(s) 150 can now provide an easy-to-comply customized and yet dynamic nutritional plan for the beneficiary while providing the macronutrients and micronutrients (see screenshots 300G of FIG. 3G and step 250).

Beneficiary options for formulations of nutritional plans may range general recommendations to very specific meals, e.g., dinner comprising of three ounces of baked fish, five ounces of steamed broccoli, half cup of steamed brown rice, three ounces of dry-roasted unsalted cashews and one fresh navel orange.

In this exemplary dinner:
three ounces of baked salmon provides macronutrients 24 grams of protein, 10 grams of fat, and micronutrients 4% of daily vitamin A daily requirements, 4% of vitamin C daily requirements, and 2% of calcium daily requirements;
five ounces of steamed broccoli provides 0.64 gram of fat, 11 grams of carbohydrates, 5.2 grams of dietary fiber, 13% of vitamin A daily requirements, 135% of vitamin C daily requirements, 245% of vitamin K daily dietary requirements, 42% of folate daily dietary requirements;
half cup of steamed brown rice provides 0.8 gram of fat, 22 grams of carbohydrates, 1.7 grams of dietary fiber, 0% of vitamin A daily requirements, 0% of vitamin C daily requirements, 1% of vitamin K daily dietary requirements, 2% of folate daily dietary requirements;
three ounces of dry-roasted unsalted cashews provides 46 gram of fat, 30 grams of carbohydrates, 3.2 grams of dietary fiber, 0% of vitamin A daily requirements, 0% of vitamin C daily requirements, 42% of vitamin K daily dietary requirements, 6% of folate daily dietary requirements; and
one fresh navel orange provides 0.2 gram of fat, 21 grams of carbohydrates, 4.3 grams of dietary fiber, 8% of vitamin A daily requirements, 160% of vitamin C daily requirements, 0% of vitamin K daily dietary requirements, 14% of folate daily dietary requirements.

Figure 3H:
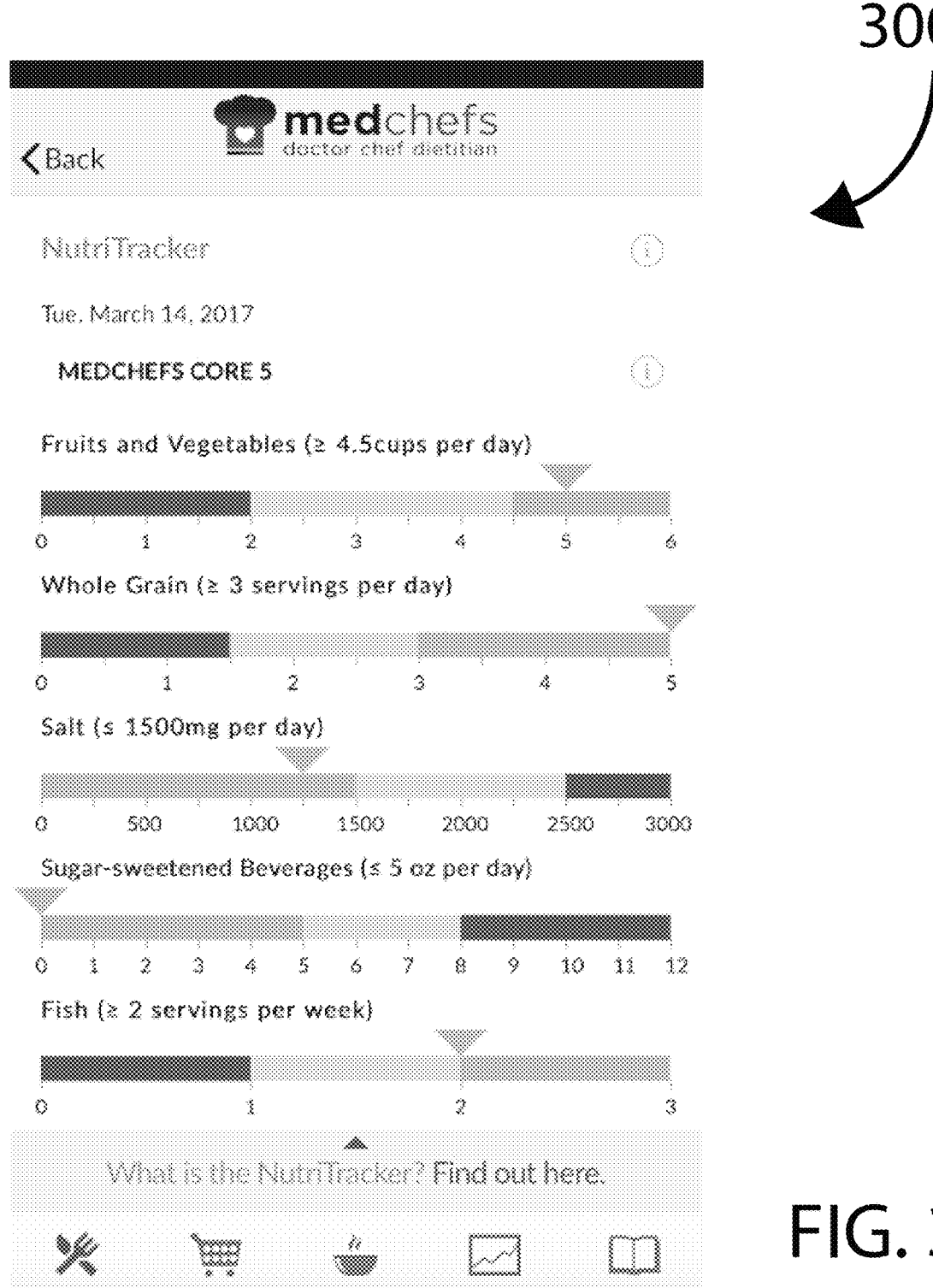

An objective score for the nutritional plan can be displayed thereby providing positive motivation to the beneficiary (see screenshot 300H illustrating an exemplary NutriTracker feature as shown in FIG. 3H). In this example, servings of fruits and vegetables, whole grains, salt, sugar and fish are tracked.

Figure 3J:
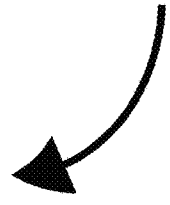
Figure 3K:
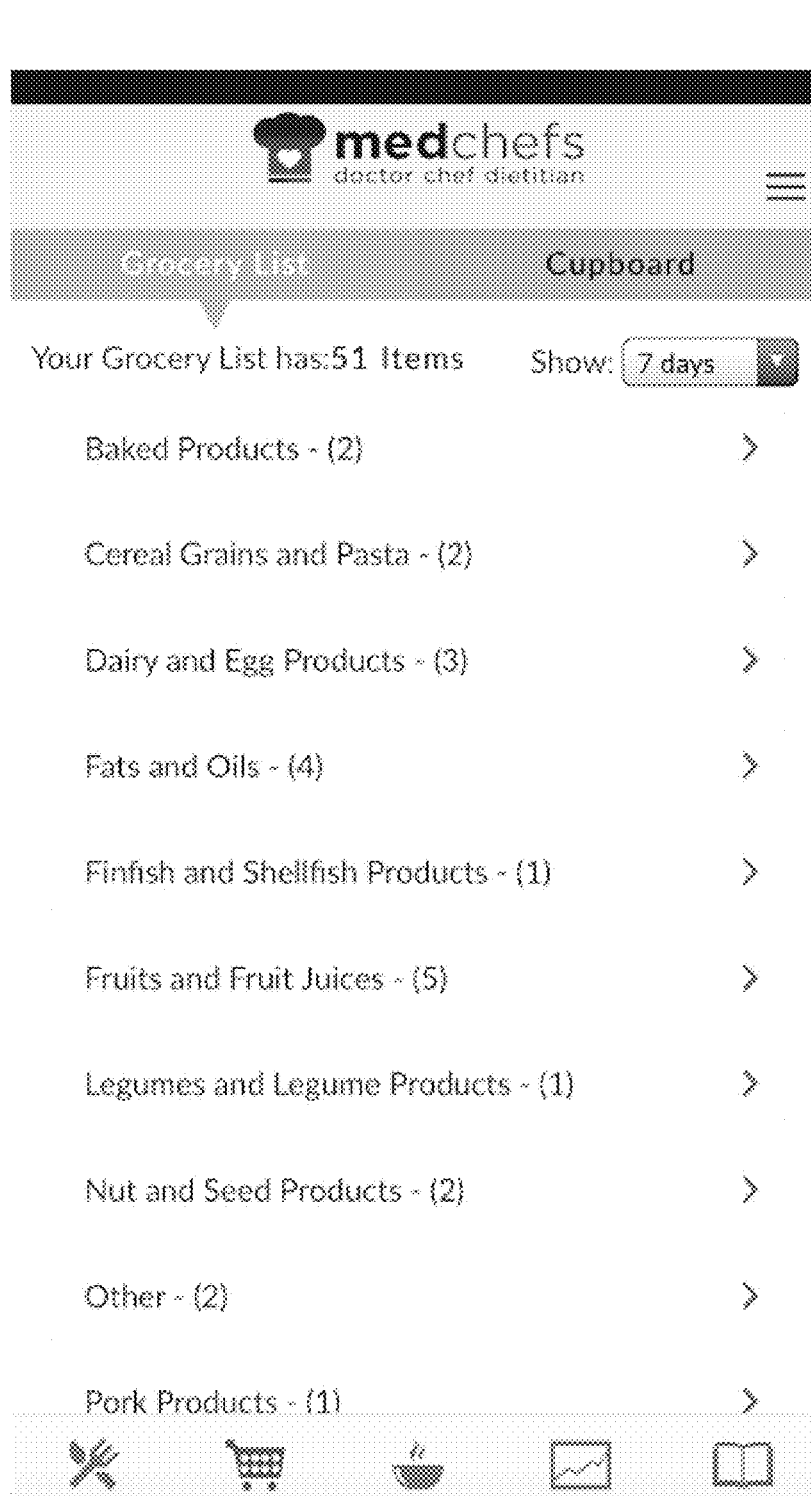

As illustrated by screenshots 300J-300K of FIGS. 3J-3K, in some embodiments, the MedChefs Server(s) 150 can also provide helpful recipe(s) and grocery list(s), respectively.

The grocery list may also be categorized into food categories/types for ease of nutritional tracking, including but not limited to macronutrient categories. The grocery list can be divided into Food Group categories for shopping convenience, and further broken down into specific groups such as baked products, cereal grains and pasta, daily and egg products, fats and oils, finfish and shellfish, fruits, legumes, nuts and meats. Note that food can be packaged and preserved in many forms, including fresh, chilled, frozen, freeze-dried, smoked, canned, or bottled.

Nutritional resources such as helpful nutritional information may also be provided to the nutritional beneficiaries and/or caregivers in the form of studies written for the lay population and based on real science, as exemplified by screenshot 300L of FIG. 3L. To protect beneficiaries from potential harmful misinformation, the MedChefs Server(s) 150 screens and vets article(s) based on anecdotal evidence prior to dissemination.

Figure 3M:
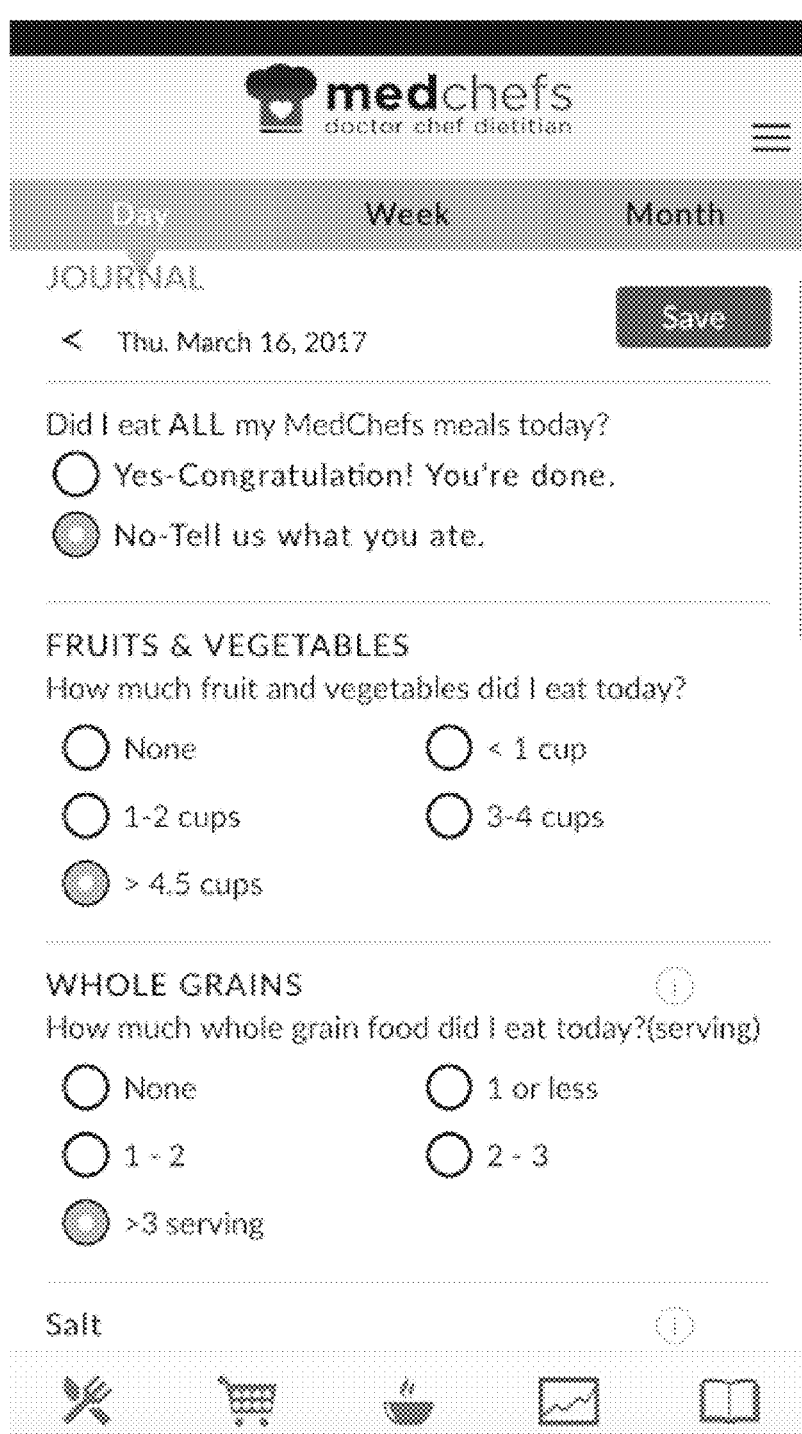
Figure 3N:
Figure 4:
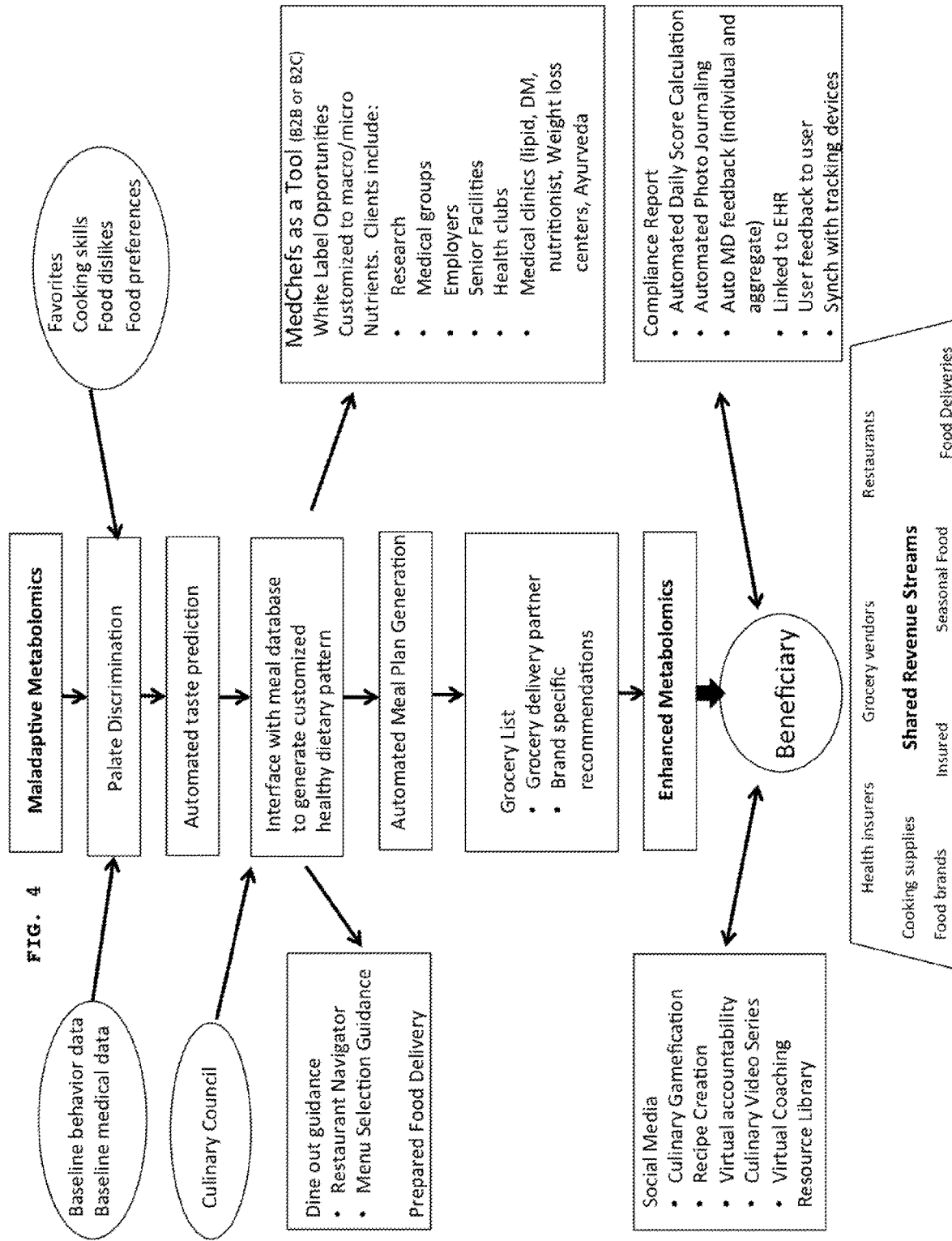
FIG. 4 is another block diagram illustrating workflow and potential partnerships for the MedChefs Ecosystem of FIG. 1.

In steps 260 & 270, the nutritional plan for the beneficiary can be periodically adjusted in response to compliance feedback for example, by compiling a journal which includes the beneficiary's intake of sodium, sweetened beverages, fish, and fiber (see screenshots 300M-300N of FIGS. 3M-3N. Referring also to FIG. 4, in some embodiments, the Enhanced Metabolomics workflow includes capability for automatically calculating a periodic score within a Compliance Report.

Figure 3P:
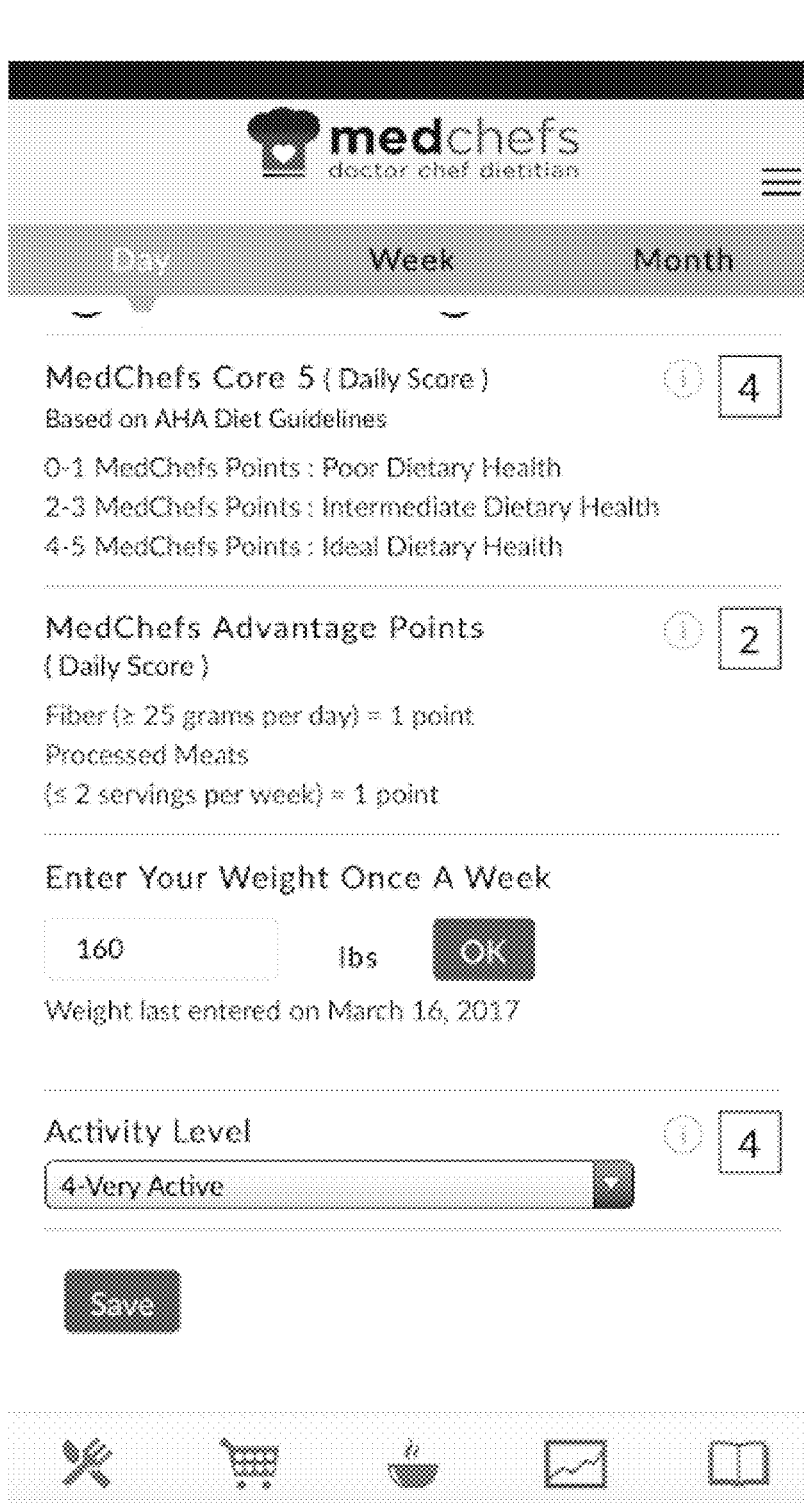

Screenshot 300P of FIG. 3P illustrates the capability to substantially improve beneficiary compliance to the nutritional plan by providing reinforcing positive feedback in the form of exemplary NutriTracker's MedChefs Core5 Scores based on MedChefs Advantage Points. Additional forms of positive reinforcement can include financial incentives such as reward points redeemable at facilitators such as grocery stores.

The MedChefs recommendations are generally based on well-researched science such the American Heart Association (AHA) Dietary Guideline and AHA dietary score. In one embodiment, NutriTracker of MedChefs Ecosystem 100 awards the metabolomic beneficiary with Core 5 and/or Advantage Points as follows:
1 Point for >4.5 cups of fruits and vegetables per day;
1 Point for >3 servings of whole grains per day;
1 Point for at least 2 servings of fish per week;
1 Point for <1,500 mg of sodium per day;
1 Point for <36 ounces of sweet beverages per week;
1 Point for <2 servings per week of processed meats; and
1 Point for >25 grams of dietary fiber for women, or >38 grams of dietary fiber for men.

In some embodiments, user interfaces of MedChefs Server(s) 150 are configured to accommodate sales/marketing information, e.g., paid advertisements with or without embedded web links, originating from MedChefs Server(s) 150 and/or Third party Server(s) 170. Such sales/marketing information can potentially generate revenue for supporting the operations of MedChefs Server(s) 150.

Many other modifications and additions to the above described embodiments are possible. For example, recommendations can include recipes that promote health while suggesting spices or seasonings such as turmeric, ginger, onions, lemon and garlic to enhance flavors preferred by the metabolomic beneficiary while substituting and/or minimizing potentially harmful additives such as salt and sugars and stimulants such as caffeine.

MedChefs Servers 150 can also be operatively coupled to partners via Third Party Servers 170. Partnerships include any entity with financial risk for the health of a population.

In other words any stakeholder including medical groups and hospitals, employers, public health services, and insurance companies. As illustrated by FIG. 4, potential partners can also include grocery stores, health clubs, senior facilities, medical groups, and hospitals.

Additional possible MedChefs auxiliary partners may include pet food stores to save on delivery costs. Other auxiliary partners can include dog walking services, janitorial services, chauffeur services, gardening/landscaping services (enabling organic farming at home), emergency food suppliers, restaurants, hotels, farmers markets, delivery services, airlines (especially international carriers), book-a-chef services, caterers, trains, cruise lines, ferries, buses, limo services, ride sharing services, and self-driving vehicular services.

MedChefs Ecosystem 100 may also encompass partnerships with online social networks such as FaceBook™. One exemplary use of social networking partnerships is to enable friends/family of a recuperating, ailing or grieving beneficiary to coordinate food drops for the beneficiary and/or her/his immediate family member(s), especially if they are minors or disabled.

As such, potential partners include any potential direct and indirect revenue generators, for example, amateur and professional athletic organizations seeking to optimize athletic performance by using the MedChefs Ecosystem 100 to "dial in" precise event-specific nutritional requirements. Other potential partnerships can also include non-profit, governmental and quasi-governmental organizations, such as Red Cross™ Red Crescent™, State Office of Emergency Services, and FEMA.

It is also contemplated that MedChefs Ecosystem 100 will serve a very wide range of beneficiaries. For active beneficiaries, MedChefs Ecosystem 100 can partner with operators/guides of campsites, backpackers, cross country skiers, mountain climbers, to for example provide high-calorie freeze-fried foods. MedChefs Ecosystem 100 can also serve patients with chronic and/or physiological conditions such as eating disorders (e.g., bulimia and anorexia).

Since MedChefs Ecosystem 100 has the ability for highly personalized interaction with individual metabolomic beneficiaries and/or their caregivers, it may also be possible to for Ecosystem 100 to support clinical studies that include food as a component.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computerized method designed to customize a healthy dietary pattern metabolomic regiment specifically to prevent and/or reverse at least one diet-related disease is provided, wherein the diet-related disease includes at least one of hypertension, diabetes mellitus, dyslipidemias, cardiovascular disease, stroke, kidney disease, liver disease and some cancers, and wherein customization of the healthy dietary metabolomic regiment is achieved by a computerized system and is unique to the beneficiary, the method comprising:
   receiving characteristics of the beneficiary associated with a metabolic beneficiary;
   receiving pabulum preferences associated with the metabolic beneficiary including baseline behavior data;
   identifying specific foods for exclusion from a superset of foods based on the pabulum preferences;
   generating an automated taste prediction utilizing the pabulum preferences derived from the baseline behavior data;
   generating a unique palate signature for the beneficiary based on the automated taste prediction;
   generating an individualized healthy dietary metabolomic regiment to enhance metabolomics of the beneficiary, wherein the individualized healthy dietary metabolomic regiment excludes the identified foods, is extracted from a comprehensive nutrition database, the individualized healthy dietary metabolomic regiment enhances metabolomics of the beneficiary based on the beneficiary characteristics and the unique palate signature;
   wherein the comprehensive nutrition database provides the beneficiary with the healthy dietary metabolomic regiment:
      maximizing healthy foods which include minimally processed and plant-based foods with sufficient dietary fiber from fruits, vegetables and whole grains; and
      minimizing unhealthy foods which include, sweetened beverages, highly processed food and salt;
   optimizing health outcomes of the beneficiary by providing the individualized healthy metabolomic regiment to the beneficiary for prevention of dietary-related diseases, and wherein the individualized healthy metabolomic regiment includes:
      4.5 or more cups of fruits and vegetables per day;
      3 or more servings of whole grains per day;
      at least 2 servings of fish per week;
      less than 1,500 mg of sodium per day;
      less than 36 ounces of sweet beverages per week;
      less than 2 servings per week of processed meats; and
      greater than 25 grams of dietary fiber;
   computing a rating of compliance to the individualized healthy metabolomic regiment by the beneficiary, wherein the computation of the rating of compliance includes tracking a journal maintained by the beneficiary, and wherein the journal includes a compilation of food consumed by the beneficiary wherein the rating of compliance includes a score based on a degree of adherence to the individualized healthy metabolomic regiment, wherein the score includes at least one point for each of at least the following:
      consumption of greater than 4.5 cups of fruit and vegetables per day;
      consumption of greater than 3 servings of whole grains per day;
      consumption of less than 1500 mg of salt per day;
      consumption of less than 5 oz of sweetened beverages per day;
      consumption of greater than 2 servings of fish per week; and
      wherein the score includes bonus points, for each of the following:
         consumption of greater than 25 grams of fiber per day; and consumption of less than 2 servings of processed meats per week;

periodically adjusting the individualized healthy metabolomic regiment responsive to the score being above a predefined threshold that is to achieve an ideal dietary health, and is responsive to the pabulum preferences of the individual, wherein the computerized system creates, in an automated fashion the dietary metabolomic regiment, customized to the beneficiary's pabulum preferences and maintaining the score above the threshold for the purpose of preventing and/or reversing at least one diet-related disease;

providing the rating of compliance to the beneficiary and to a stakeholder; and enabling the stakeholder to give positive reinforcing compliance feedback to the beneficiary and wherein the stakeholder iteratively makes the periodic adjustments to the individualized healthy metabolomic regiment to increase the rating of compliance, thereby enhancing the metabolomics of the beneficiary in a personalized manner to prevent and/or reverse the at least one diet-related disease, and wherein the computerized system is scalable for a general population.

2. The method of claim 1 wherein the beneficiary characteristics include physiological data of the beneficiary including at least one of age, gender, weight, height, ethnic composition, and body-fat-to-muscle ratio (BMI).

3. The method of claim 2 wherein the physiological data of the beneficiary includes metabolic metrics lipid data and glucose levels.

4. The method of claim 2 wherein the physiological data of the beneficiary includes hemodynamic data including blood pressure.

5. The method of claim 2 wherein the physiological data of the beneficiary includes endothelial function assessments.

6. The method of claim 2 wherein the physiological data of the beneficiary includes noninvasive markers of atherosclerosis including ultrasound derived intimal medial thickness measurements.

7. The method of claim 1 wherein the beneficiary has a medical condition consisting of at least one of cardiovascular disease, hypertension, cancer, diabetes, allergy, and genetic predispositions.

8. The method of claim 1 wherein the dietary metabolomic regiment include proteins, carbohydrates and fats, vitamins and minerals.

9. The method of claim 1 further comprising providing pabulum choices including seafood, fruits, vegetables, nuts, whole grain, and dietary fiber.

10. The method of claim 1 wherein the individualized healthy metabolomic regiment includes at least one of seasonal pabulum and local pabulum.

11. The method of claim 1 further comprising receiving lifestyle data of the beneficiary including at least one of a physical activity and a mental activity.

12. The method of claim 11 wherein the physical activity is received from a wearable device and wherein the physical activity includes caloric expenditure from exercise.

13. The method of claim 1 wherein providing the individualized healthy metabolomic regiment includes providing a pabulum plan including at least one of a menu choice, a recipe, and a grocery shopping list.

14. The method of claim 13 further comprising providing the pabulum plan to at least one of the beneficiary, a healthcare provider, a caregiver, a dietary provider and an athletic training program manager.

15. The method of claim 13 further comprising providing the rating of compliance to at least one of the beneficiary and a third party, and wherein the third party includes at least one of a healthcare provider, a caregiver, a dietary provider and an athletic training program manager.

16. The method of claim 15 wherein the rating of compliance is provided to the third party via a social network, thereby facilitating beneficiary with encouragement to substantially improve compliance with the pabulum plan.

17. The method of claim 1 further comprising receiving supplemental compliance data from a third party via a social network.

18. The method of claim 1 further comprising:
receiving an update of the beneficiary characteristics; and
updating the individualized healthy metabolomic regiment in accordance with the updated beneficiary characteristics.

19. The method of claim 1 wherein the individualized healthy metabolomic regiment results in primordial prevention.

20. The method of claim 1 further comprising of transmitting the individualized healthy metabolomic regiment to one or more partners.

21. The method of claim 20 wherein the one or more partners includes at least one of a restaurant, a food delivery service, a transportation provider, and an establishment providing accommodations.

22. The method of claim 1 wherein the compliance feedback includes a core score and an advantage score based on the scientifically researched guidelines and the rating of compliance.

23. The method of claim 1 wherein the scientifically researched guidelines include the American Heart Association (AHA) guidelines.

24. The method of claim 1 wherein the prevention of diet-related diseases includes primordial prevention, primary prevention and secondary prevention.

25. The method of claim 1, wherein the threshold is at least four.

* * * * *